United States Patent
Shin et al.

(10) Patent No.: US 10,538,539 B2
(45) Date of Patent: Jan. 21, 2020

(54) METHOD FOR PREPARING 3-((2S, 5S)-4-METHYLENE-5-(3-OXOPROPYL) TETRAHYDROFURANE-2-YL) PROPANOL DERIVATIVE, AND INTERMEDIATE THEREFOR

(71) Applicant: YONSUNG FINE CHEMICAL CO., LTD., Hwaseong-si, Gyeonggi-do (KR)

(72) Inventors: Hyun Ik Shin, Yongin-si (KR); Kee Young Lee, Seoul (KR); Changyoung Oh, Seongnam-si (KR)

(73) Assignee: YONSUNG FINE CHEMICAL CO., LTD., Hwaseong-si (KR)

( * ) Notice: Subject to any disclaimer, the term of this patent is extended or adjusted under 35 U.S.C. 154(b) by 0 days.

(21) Appl. No.: 16/070,669

(22) PCT Filed: Jan. 13, 2017

(86) PCT No.: PCT/KR2017/000449
§ 371 (c)(1),
(2) Date: Jul. 17, 2018

(87) PCT Pub. No.: WO2017/126847
PCT Pub. Date: Jul. 27, 2017

(65) Prior Publication Data
US 2019/0023727 A1 Jan. 24, 2019

(30) Foreign Application Priority Data
Jan. 18, 2016 (KR) .................. 10-2016-0005957

(51) Int. Cl.
*C07F 7/18* (2006.01)
(52) U.S. Cl.
CPC .......... *C07F 7/1892* (2013.01); *C07F 7/1804* (2013.01)
(58) Field of Classification Search
CPC .............................. C07F 7/1804; C07F 7/1872

USPC ......................................................... 549/214
See application file for complete search history.

(56) References Cited

U.S. PATENT DOCUMENTS

| 5,081,136 A | 1/1992 | Bertolini et al. |
| 5,436,238 A | 7/1995 | Kishi et al. |

FOREIGN PATENT DOCUMENTS

| KR | 10-1434673 B1 | 8/2014 |
| WO | 2005/118565 | 12/2005 |
| WO | 2013/086634 A1 | 6/2013 |
| WO | 2014/183211 A1 | 11/2014 |

OTHER PUBLICATIONS

Alistair Boyer, "Rhodium (II)-Catalyzed Stereocontrolled Synthesis of Dihydrofuran-3-imines from 1-Tosyl-1,2,3-triazoles", Organic Letters, 2014, pp. 1660-1663, vol. 16, No. 6.
Thanos Andreou, et al., "Synthesis of (−)-Amphidinolide K Fragment C9-C22", Organic Letters, 2005, pp. 4083-4086, vol. 7, No. 19.
Margaret A. Brimble, et al., Synthesis of the spiroacetal fragment of broussonetine H, Tetrahedron, 2003, pp. 5861-5868, vol. 59.
International Searching Authority, International Search Report for PCT/KR2017/000449 dated Apr. 26, 2017 [PCT/ISA/210].
Jackson et al., "A Total Synthesis of Norhalichondrin B", Angew. Chem. Int. Ed., vol. 48, No. 13, 2009, pp. 2346-2350.
Alistair Boyer, "Enantioselective Synthesis of (+)-Petromyroxol, Enabled by Rhodium-Catalyzed Denitrogenation and Rearrangement of a 1-Sulfonyl-1,2,3-Triazole", J. Org. Chem., vol. 80, 2015, pp. 4771-4775.

*Primary Examiner* — Matthew P Coughlin
*Assistant Examiner* — Sagar Patel
(74) *Attorney, Agent, or Firm* — Sughrue Mion, PLLC

(57) ABSTRACT

A method for preparing a 3-((2S,5S)-4-methylene-5-(3-oxopropyl)tetrahydrofuran-2-yl)propanol derivative by a simple process with high yields, and an intermediate useful for the method.

8 Claims, No Drawings

METHOD FOR PREPARING 3-((2S, 5S)-4-METHYLENE-5-(3-OXOPROPYL) TETRAHYDROFURANE-2-YL) PROPANOL DERIVATIVE, AND INTERMEDIATE THEREFOR

CROSS REFERENCE TO RELATED APPLICATIONS

This application is a National Stage of International Application No. PCT/KR2017/000449 filed Jan. 13, 2017, claiming priority based on Korean Patent Application No. 10-2016-0005957 filed Jan. 18, 2016.

TECHNICAL FIELD

The present invention relates to a process for preparing a 3-((2S,5S)-4-methylene-5-(3-oxopropyl)tetrahydrofuran-2-yl)propanol derivative and an intermediate therefor. More particularly, the present invention relates to a process for preparing a 3-((2S,5S)-4-methylene-5-(3-oxopropyl)tetrahydrofuran-2-yl)propanol derivative by a simple process with high yields, and an intermediate therefor.

BACKGROUND ART 3-((2S,5S)-4-methylene-5-(3-oxopropyl)tetrahydrofuran-2-yl)propanol derivatives have the structure of the following formula (1), and have been effectively used as intermediates for C14-C23 moiety in the preparation of Halichondrin B of the following formula (2) and Eribulin mesylate of the following formula (3) having anti-cancer activity[see U.S. Pat. No. 5,436,238 and Korean Patent No. 10-1434673].

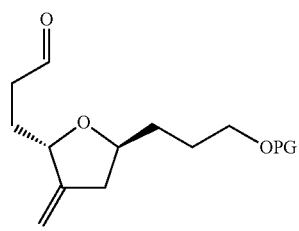

(1)

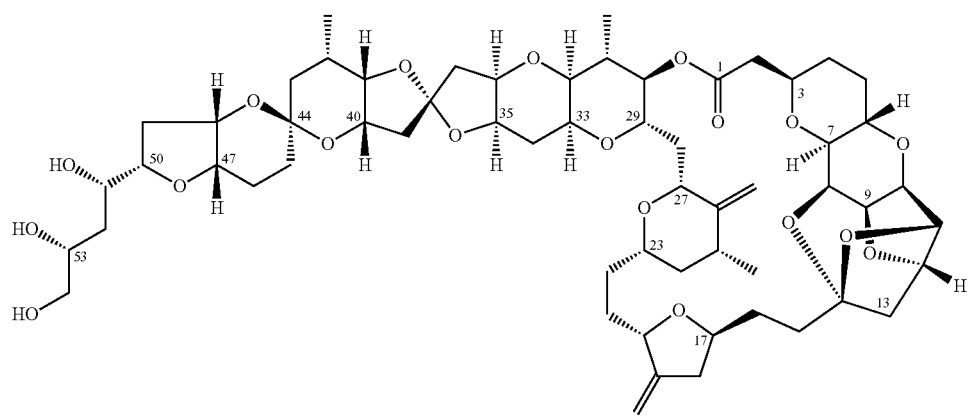

(2)

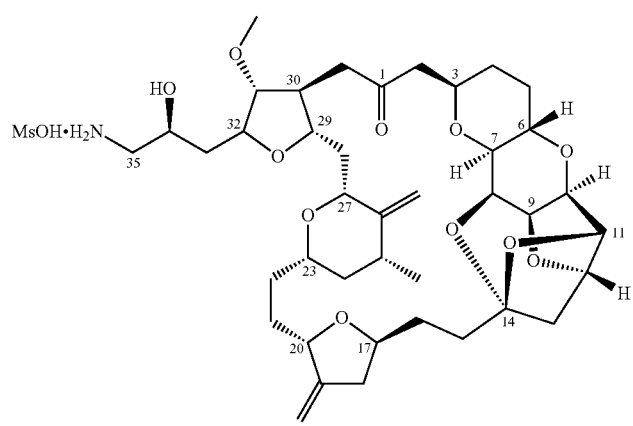

(3)

3

For the preparation of the 3-((2S,5S)-4-methylene-5-(3-oxopropyl)tetrahydrofuran-2-yl)propanol derivatives of formula (1), various synthesis processes have been reported, but most of them have problems of an excessively long synthetic pathway and low yields.

For example, the preparation process disclosed in Korean Patent No. 10-1434673 includes ozonolysis, hydrogenation, and repeated protections and deprotections, so it is inefficient and has long reaction steps, thereby being difficult to be industrialized.

Further, Wo2014/183211A1 discloses that the 3-((2S,5S)-4-methylene-5-(3-oxopropyl)tetrahydrofuran-2-yl)propanol derivatives of formula (1) can be prepared through the synthetic steps of the following Reaction Scheme 1.

[Reaction Scheme 1]

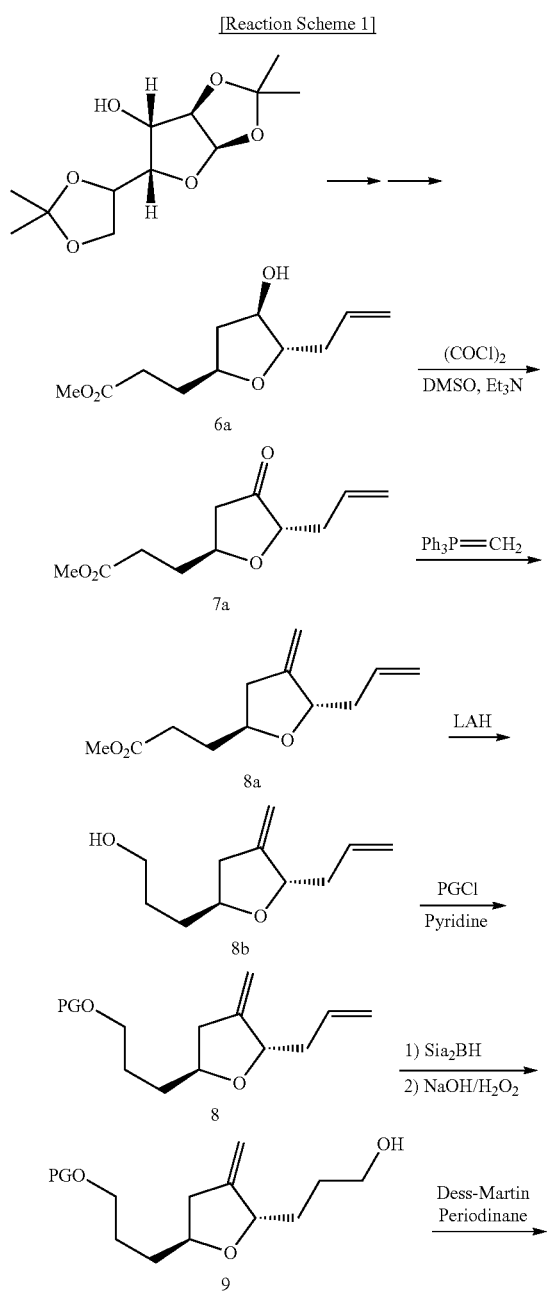

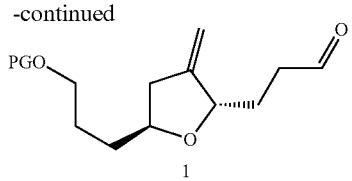

However, compound 6a produced in Reaction Scheme 1 is difficult to be separated because an epimer is formed due to low stereoselectivity in position 2 of the furan ring.

Therefore, there has been a need to develop a process capable of preparing the 3-((2S,5S)-4-methylene-5-(3-oxopropyl)tetrahydrofuran-2-yl)propanol derivatives of formula (1) by a simple process with high yields.

DISCLOSURE

Technical Problem

The present inventors have endeavored to overcome the above problems of the preparation of the 3-((2S,5S)-4-methylene-5-(3-oxopropyl)tetrahydrofuran-2-yl)propanol derivatives, and found that the target compounds can be simply prepared with high yields by using a triazole compound as an intermediate.

An object of the present invention is, therefore, to provide a process for preparing a 3-((2S,5S)-4-methylene-5-(3-oxopropyl)tetrahydrofuran-2-yl)propanol derivative by a simple process with high yields.

Another object of the present invention is to provide an intermediate used in the above preparation process.

Technical Solution

One embodiment of the present invention relates to a process for preparing a 3-((2S,5S)-4-methylene-5-(3-oxopropyl)tetrahydrofuran-2-yl)propanol derivative of the following formula (1), which comprises the steps of:

(i) reacting a compound of the following formula (4) with allyl bromide to obtain a compound of the following formula (5);

(ii) reacting the compound of the following formula (5) with an arylsulfonyl azide to obtain a triazole compound of the following formula (6);

(iii) subjecting the triazole compound of the following formula (6) to denitrification and rearrangement followed by hydrolysis to obtain a tetrahydrofuran compound of the following formula (7);

(iv) subjecting the tetrahydrofuran compound of the following formula (7) to Wittig reaction to obtain a compound of the following formula (8);

(v) subjecting the compound of the following formula (8) to hydroboration followed by oxidation to obtain a compound of the following formula (9); and (vi) oxidizing a hydroxyl group of the compound of the following formula (9):

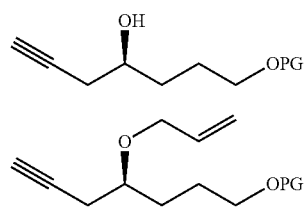

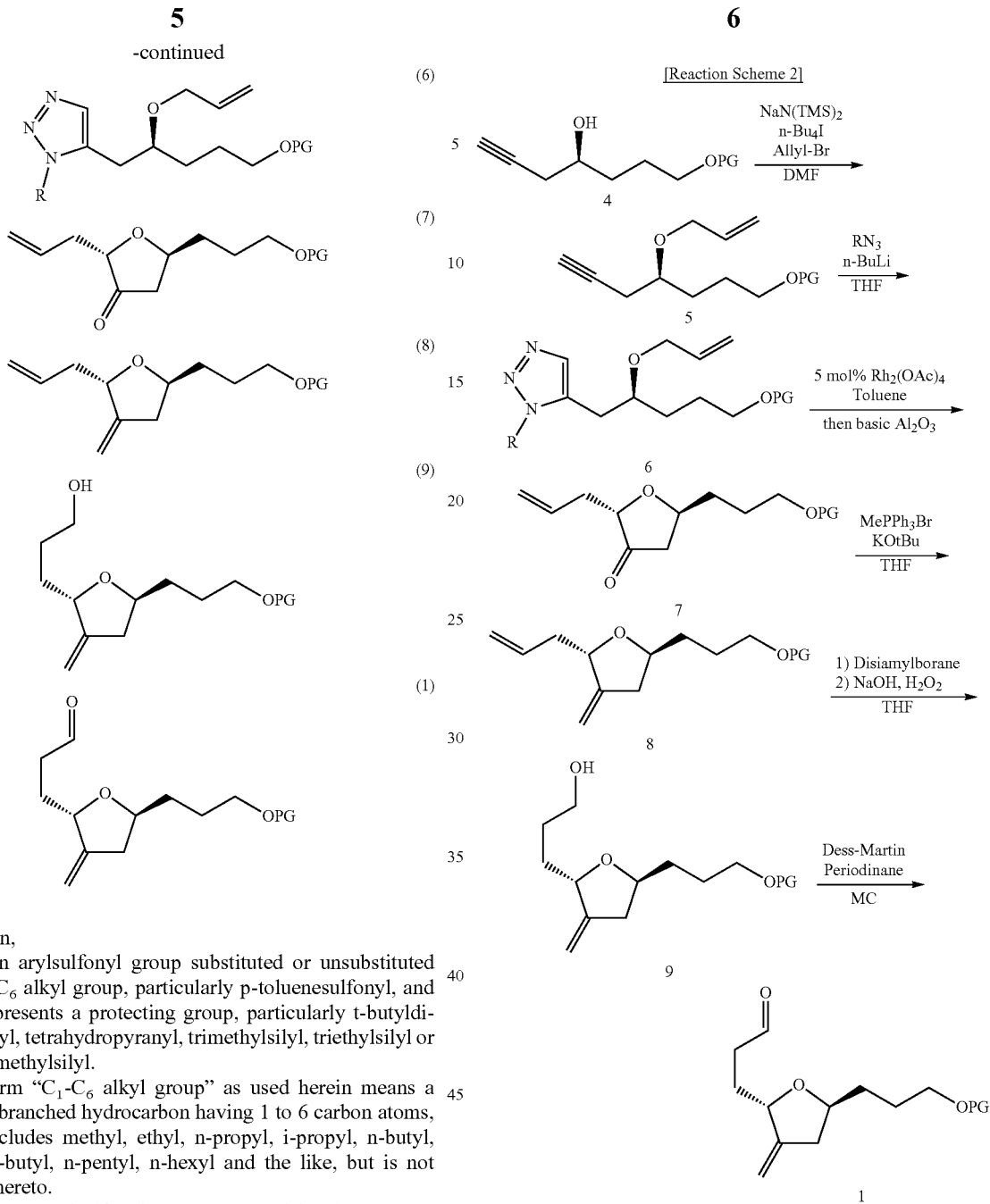

wherein,

R is an arylsulfonyl group substituted or unsubstituted with $C_1$-$C_6$ alkyl group, particularly p-toluenesulfonyl, and PG represents a protecting group, particularly t-butyldiphenylsilyl, tetrahydropyranyl, trimethylsilyl, triethylsilyl or t-butyldimethylsilyl.

The term "$C_1$-$C_6$ alkyl group" as used herein means a linear or branched hydrocarbon having 1 to 6 carbon atoms, which includes methyl, ethyl, n-propyl, i-propyl, n-butyl, i-butyl, t-butyl, n-pentyl, n-hexyl and the like, but is not limited thereto.

The term "arylsulfonyl group" as used herein means a sulfonyl group (—$SO_2$—) substituted with an aryl group, and the aryl group includes all of an aromatic group, a heteroaromatic group, and partially reduced derivatives thereof. The aromatic group means a 5 to 15-membered simple or fused ring. The heteroaromatic group means an aromatic group containing at least one atom selected from oxygen, sulfur and nitrogen. Representative examples of the aryl group include phenyl, naphthyl, pyridinyl, furanyl, thiophenyl, indolyl, quinolinyl, imidazolinyl, oxazolyl, thiazolyl, tetrahydronaphthyl and the like, but are not limited thereto.

The process of the present invention is, hereinafter, described in more detail referring to the following Reaction Scheme 2. The process depicted in the following Reaction Scheme 2 represents merely a typical example, and various changes may be made to reagents and reaction conditions without limitation.

Step 1: Synthesis of Compound of Formula (5)

The compound of formula (5) can be obtained by reacting the compound of formula (4) with allylbromide in the presence of a base.

The base may be sodium bis(trimethylsilyl)amide, potassium bis(trimethylsilyl)amide, lithium bis(trimethylsilyl)amide, etc., preferably sodium bis(trimethylsilyl)amide.

Also, the above reaction can be performed in the presence of n-tetrabutylammonium iodide as a catalyst.

The reaction is preferably performed at the temperature of 0 to 25° C. for 3 to 6 hours.

As the reaction solvent, polar solvents which do not affect the reaction can be used, and specific examples thereof include dimethylformamide, tetrahydrofuran, methylenechloride, toluene, etc. In particular, dimethylformamide is preferred.

Meanwhile, the compound of formula (4) used as a starting material can be easily synthesized by a known process [see Org. Lett. 2005, 7, 19, 4083-4086; Tetrahedron 2003, 59, 5861-5868] or is commercially available.

Step 2: Synthesis of Compound of Formula (6)

The triazole compound of formula (6) can be obtained by reacting the compound of formula (5) with an arylsulfonyl azide ($RN_3$) in the presence of a base.

The base may be n-butyl lithium, t-butyl lithium, methyl lithium, etc., preferably n-butyl lithium.

The reaction is preferably performed at the temperature of −78 to −20° C. for 30 minutes to 4 hours.

As the reaction solvent, polar solvents which do not affect the reaction can be used, and specific examples thereof include tetrahydrofuran, methylenechloride, toluene, etc. In particular, tetrahydrofuran is preferred.

Step 3: Synthesis of Compound of Formula (7)

The compound of formula (7) can be obtained by subjecting the triazole compound of formula (6) to denitrification and rearrangement, followed by hydrolysis.

As shown in the following Reaction Scheme 3, the denitrification and rearrangement may be sequentially performed in the presence of a rhodium catalyst, which allows the stereoselective synthesis of the tetrahydrofuran ring compound. Therefore, the compound of formula (1) can be prepared with high yields without difficulty separating a racemate.

The Wittig reaction may be performed using methyltriphenylphosphonium bromide ($MePPh_3Br$) and potassium t-butoxide (KOtBu).

The reaction is preferably performed at the temperature of 0 to 10° C. for 1 to 2 hours.

As the reaction solvent, polar solvents which do not affect the reaction can be used, and specific examples thereof include toluene, tetrahydrofuran, methylenechloride, etc. In particular, tetrahydrofuran is preferred.

Step 5: Synthesis of Compound of Formula (9)

The compound of formula (9) can be obtained by subjecting the compound of formula (8) to hydroboration followed by oxidation.

The hydroboration may be performed using disiamylborane, 9-borabicyclo[3.3.1]nonane, etc., preferably disiamylborane.

The hydroboration is preferably performed at the temperature of −20 to −10° C. for 30 minutes to 3 hours.

The oxidation may be performed using hydrogen peroxide, sodium perborate, etc. in the presence of a base. In particular, hydrogen peroxide is preferred.

The base may be sodium hydroxide, potassium hydroxide, etc., preferably sodium hydroxide.

The reaction is preferably performed at the temperature of 15 to 25° C. for 4 to 15 hours.

As the reaction solvent, polar solvents which do not affect the reaction can be used, and specific examples thereof

[Reaction Scheme 3]

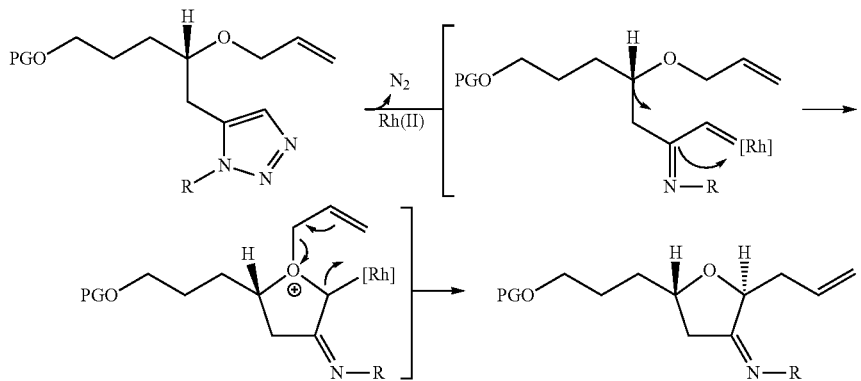

The rhodium catalyst may be dirhodium(II) tetraacetate, dirhodium(II) carboxylate, dirhodium(II) carboxamidate, etc., preferably dirhodium(II) tetraacetate.

The denitrification and rearrangement is preferably performed under reflux condition for 0.5 to 2 hours.

The compound of formula (7) can be obtained by subjecting the imine compound produced by the denitrification and rearrangement to hydrolysis in the presence of alumina ($Al_2O_3$).

The hydrolysis is preferably performed at room temperature for 0.5 to 1 hour.

As the reaction solvent used in the denitrification and rearrangement and the hydrolysis, polar solvents which do not affect the reaction can be used, and specific examples thereof include toluene, tetrahydrofuran, methylenechloride, etc. In particular, toluene is preferred.

Step 4: Synthesis of Compound of Formula (8)

The compound of formula (8) can be obtained by subjecting the compound of formula (7) to Wittig reaction.

include tetrahydrofuran, methylenechloride, toluene, etc. In particular, tetrahydrofuran is preferred.

Step 6: Synthesis of Compound of Formula (1)

The target compound of formula (1) can be obtained by oxdizing the hydroxyl group of the compound of formula (9).

The oxidation may be performed using Dess-Martin periodinane, Swern oxidation, Collins reagent, pyridinium dichromate (PDC), Pfitzner-Moffatt oxidation, Parikh-Doering oxidation, Ley oxidation, etc., preferably Dess-Martin periodinane.

The oxidation is preferably performed at the temperature of 15 to 30° C. for 1 to 4 hours.

As the reaction solvent, polar solvents which do not affect the reaction can be used, and specific examples thereof include methylenechloride, tetrahydrofuran, toluene, etc. In particular, methylenechloride is preferred.

One embodiment of the present invention relates to a compound of the following formula (6) which is an intermediate for the preparation of the compound of formula (1):

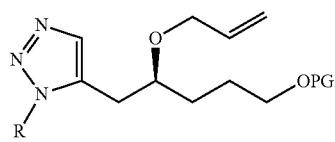

(6)

wherein,

R is an arylsulfonyl group substituted or unsubstituted with $C_1$-$C_6$ alkyl group, particularly p-toluenesulfonyl, and PG represents a protecting group, particularly t-butyldiphenylsilyl, tetrahydropyranyl, trimethylsilyl, triethylsilyl or t-butyldimethylsilyl.

One embodiment of the present invention relates to a process for preparing the compound of the following formula (6), which comprises the steps of:

(i) reacting a compound of the following formula (4) with allyl bromide to obtain a compound of the following formula (5); and (ii) reacting the compound of the following formula (5) with an arylsulfonyl azide:

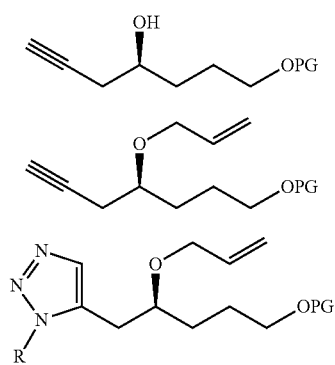

(4)

(5)

(6)

wherein,

R is an arylsulfonyl group substituted or unsubstituted with $C_1$-$C_6$ alkyl group, particularly p-toluenesulfonyl, and PG represents a protecting group, particularly t-butyldiphenylsilyl, tetrahydropyranyl, trimethylsilyl, triethylsilyl or t-butyldimethylsilyl.

The process for preparing the compound of formula (6) includes the same steps 1 and 2 as in the above process for preparing the compound of formula (1), and thus a detailed description thereof will be omitted.

One embodiment of the present invention relates to a process for preparing the compound of the following formula (1), which comprises the steps of:

(iii) subjecting a triazole compound of the following formula (6) to denitrification and rearrangement followed by hydrolysis to obtain a tetrahydrofuran compound of the following formula (7);

(iv) subjecting the tetrahydrofuran compound of the following formula (7) to Wittig reaction to obtain a compound of the following formula (8);

(v) subjecting the compound of the following formula (8) to hydroboration followed by oxidation to obtain a compound of the following formula (9); and (vi) oxidizing a hydroxyl group of the compound of the following formula (9):

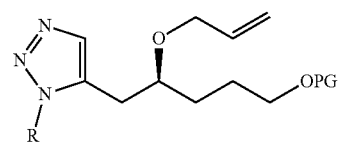

(6)

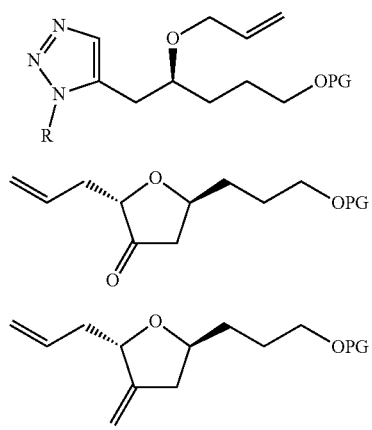

(7)

(8)

(9)

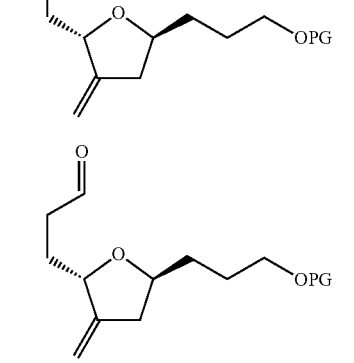

(1)

wherein,

R is an arylsulfonyl group substituted or unsubstituted with $C_1$-$C_6$ alkyl group, particularly p-toluenesulfonyl, and PG represents a protecting group, particularly t-butyldiphenylsilyl, tetrahydropyranyl, trimethylsilyl, triethylsilyl or t-butyldimethylsilyl.

The preparation process includes the same steps 3 to 6 as in the above process for preparing the compound of formula (1), and thus a detailed description thereof will be omitted.

Advantageous Effects

In accordance with the process of the present invention, the 3-((2S,5S)-4-methylene-5-(3-oxopropyl)tetrahydrofuran-2-yl)propanol derivative of formula (1) can be prepared by a simple process with high yields using the triazole compound of formula (6) as an intermediate.

BEST MODE

The present invention will be described in more detail by following examples. It will be obvious to those skilled in the art that these examples are merely described for illustration of the present invention and the scope of the present invention is not limited thereto.

Example 1: Synthesis of Compound of Formula (5)

(4S)-7-(t-butyldiphenylsilyloxy)hept-1-yn-4-ol (6.74 g) was dissolved in N,N-dimethylformamide (167 ml), and the resulting solution was cooled to 0° C. Then, sodium bis(trimethylsilyl)amide (27.58 ml), allylbromide (2.46 ml), and n-tetrabutylammonium iodide (2.08 g) were sequentially added thereto. The resulting solution was slowly warmed to room temperature and stirred for 6 hours. A saturated aqueous solution of ammonium chloride was added to the resulting solution to complete the reaction, followed by extracting with ethyl ether. The organic layer was washed with 10 wt % lithium chloride, dried with anhydrous sodium sulfate, and then concentrated under reduced pressure. The product was purified by silica gel column chromatography to give (4S)-4-(allyloxy)-7-(t-butyldiphenylsilyloxy)hept-1-yne as yellow oil (6.56 g, 87.7%).

$^1$H NMR (300 MHz, CDCl$_3$) δ=7.68-7.65 (m, 4H), 7.42-7.34 (m, 6H), 5.88-5.84 (m, 1H), 5.29-5.22 (dd, J=17.1 Hz, 1H), 5.16-5.12 (dd, J=10.4, 1H), 4.07-4.05 (dd, 1H), 3.98-3.96 (dd, 1H), 3.70 (t, J=5.7 Hz, 2H), 3.48 (m, 1H), 2.42-2.36 (m, 2H), 1.97 (t, J=3.0 Hz, 1H), 1.70-1.63 (m, 4H), 1.05 (s, 9H).

Example 2: Synthesis of Compound of Formula (6)

(4S)-4-(allyloxy)-7-(t-butyldiphenylsilyloxy)hept-1-yne (21 g) obtained in Example 1 was dissolved in tetrahydrofuran (60 ml). The resulting solution was cooled to −78° C., and n-butyl lithium (27.6 ml, 1.93M hexane solution) was added dropwise thereto. After stirring for 10 minutes, p-toluenesulfonyl azide (103.4 ml, 11-15 w/w % toluene solution) was added dropwise, followed by stirring at −78° C. for 3 hours. A saturated aqueous solution of ammonium chloride was added to the resulting solution to complete the reaction. The resulting solution was warmed to room temperature, and then extracted with ethyl acetate. The organic layer was washed with distilled water, dried with anhydrous sodium sulfate, and then concentrated under reduced pressure. The product was purified by silica gel column chromatography to give (1S)-5-(1-allyloxy)-5-((t-butyldiphenylsilyl)oxy)butyl)-1-tosyl-1H-1,2,3-triazole as yellow oil (25.4 g, 81.5%).

$^1$H NMR (300 MHz, CDCl$_3$) δ=7.95 (d, J=8.4 Hz, 2H), 7.66 (d, J=5.7 Hz, 4H), 7.49 (s, 1H), 7.43-7.33 (m, 8H), 5.79-5.66 (m, 1H), 5.18-5.07 (m, 2H), 3.96-3.77 (m, 2H), 3.68-3.62 (m, 3H), 3.12 (d, J=6.0 Hz, 2H), 2.34 (s, 3H), 1.65-1.63 (m, 4H), 0.15 (s, 9H).

Example 3: Synthesis of Compound of Formula (7)

(1S)-5-(1-allyloxy)-5-((t-butyldiphenylsilyl)oxy)butyl)-1-tosyl-1H-1,2,3-triazole (1.4 g) obtained in Example 2 was dissolved in toluene (80 ml), and dirhodium(II) tetraacetate (0.053 g) was added thereto. The resulting solution was warmed, stirred under reflux for an hour, and then cooled to room temperature. Alumina (23.7 g, 6 wt % of water content) was added thereto, followed by stirring at room temperature for an hour. The product was purified by silica gel column chromatography to give (2S,5S)-2-allyl-5-(3-(t-butyldiphenylsilyloxy)propyl)dihydrofuran-3(2H)-one as colorless oil (0.77 g, 78.6%).

$^1$H NMR (300 MHz, CDCl$_3$) δ=7.67-7.64 (m, 4H), 7.42-7.35 (m, 6H), 5.87-5.74 (m, 1H), 5.17-5.08 (m, 2H), 4.39-4.30 (m, 1H), 4.00-3.98 (m, 1H), 3.70 (t, J=6.0 Hz, 2H), 2.57-2.15 (m, 4H), 1.80-1.56 (m, 4H), 1.05 (s, 9H).

Example 4: Synthesis of Compound of Formula (8)

Methyltriphenylphosphonium bromide (3.8 g) was added to tetrahydrofuran (22.5 ml), and the resulting solution was cooled to 0° C. or less. Potassium t-butoxide (1.2 g) was added to the resulting solution, followed by stirring at 0° C. for 1.5 hours. To the resulting solution was added dropwise (2S,5S)-2-allyl-5-(3-(t-butyldiphenylsilyloxy)propyl)dihydrofuran-3(2H)-one (1.5 g) obtained in Example 3 which was diluted in tetrahydrofuran (7.5 ml). Then, the resulting solution was stirred at 0° C. for an hour. Distilled water (15 ml) was added dropwise to the resulting solution to complete the reaction, and the resulting solution was warmed to room temperature and then extracted with ethyl acetate. The organic layer was washed with distilled water, dried with anhydrous sodium sulfate, and then concentrated under reduced pressure. The product was recrystallized with toluene and heptane, and then filtered. The filtrate was concentrated under reduced pressure to give (3-((2S,5S)-5-allyl-4-methylenetetrahydrofuran-2-yl)propoxy)t-butyldiphenylsilane as yellow oil (1.55 g). The obtained product was used for the following reaction without additional purification.

Example 5: Synthesis of Compound of Formula (9)

3-((2S,5S)-5-allyl-4-methylenetetrahydrofuran-2-yl)propoxy)t-butyldiphenylsilane (0.3 g) obtained in Example 4 was added to tetrahydrofuran (6 ml), and the resulting solution was cooled to −20° C. or less. While maintaining the temperature of −20° C. or less, disiamylborane (17.1 ml, 0.5M tetrahydrofuran solution) was added dropwise in six divisions at intervals of 30 minutes. While maintaining the temperature of 20° C. or less, 3M aqueous solution of sodium hydroxide (3 ml) and 35% hydrogen peroxide (3 ml) were sequentially added dropwise thereto. The resulting solution was stirred at room temperature for 15 hours, and extracted with ethylacetate. The organic layer was washed with saline water, dried with anhydrous sodium sulfate, and then concentrated under reduced pressure. The product was purified by silica gel column chromatography to give 3-((2S,5S)-3-methylene-5-(3-(t-butyldiphenylsilyloxy)propyl)tetrahydrofuran-2-yl)propanol as yellow oil (0.24 g, 77.4%).

$^1$H NMR (300 MHz, CDCl$_3$) δ=9.76 (t, 1H), 7.67-7.64 (m, 4H), 7.39-7.37 (m, 6H), 5.01 (d, J=2.1 Hz, 1H), 4.86 (q, J=2.1 Hz, 1H), 4.39 (d, J=8.4, 1H), 4.04-4.01 (m, 1H), 3.69-3.63 (m, 4H), 2.64 (dd, 1H), 2.57 (t, 1H), 2.25 (dd, 1H), 1.72-1.56 (m, 8H), 1.04 (s, 9H).

Example 6: Synthesis of Compound of Formula (1)

3-((2S,5S)-3-methylene-5-(3-(t-butyldiphenylsilyloxy)propyl)tetrahydrofuran-2-yl)propanol (50 mg) obtained in Example 5 was dissolved in dichloromethane (2 ml). Sodium bicarbonate (20 mg) and Dess-Martin periodinane (0.11 g) were added to the resulting solution, followed by stirring at room temperature for an hour. 25% aqueous solution of sodium thiosulfonate and saturated aqueous solution of sodium bicarbonate were added thereto to complete the reaction, followed by extraction. The organic layer was washed with saturated aqueous solution of sodium bicarbonate, dried with anhydrous sodium sulfate, and then concentrated under reduced pressure to give 3-((2S,5S)-3-methylene-5-(3-(t-butyldiphenylsilyloxy)propyl)tetrahydrofuran-2-yl)propanal as yellow oil (46 mg, 96.4%).

$^1$H NMR (300 MHz, CDCl$_3$) δ=7.67-7.64 (m, 4H), 7.40-7.37 (m, 6H), 4.99 (d, J=2.1 Hz, 1H), 4.85 (d, J=1.8 Hz, 1H), 4.41 (m, 1H), 3.98-3.96 (m, 1H), 3.69-3.66 (m, 2H), 2.62 (dd, 1H), 2.54-2.45 (m, 2H), 2.26 (dd, 1H), 1.96-1.91 (m, 1H), 1.85-1.80 (m, 1H) 1.63-1.56 (m, 4H), 1.04 (s, 9H).

The invention claimed is:

1. A process for preparing a 3-((2S,5S)-4-methylene-5-(3-oxopropyl)tetrahydrofuran-2-yl)propanol derivative of the following formula (1), which comprises the steps of:
   (i) reacting a compound of the following formula (4) with allyl bromide to obtain a compound of the following formula (5);
   (ii) reacting the compound of the following formula (5) with an arylsulfonyl azide to obtain a triazole compound of the following formula (6);
   (iii) subjecting the triazole compound of the following formula (6) to denitrification and rearrangement followed by hydrolysis to obtain a tetrahydrofuran compound of the following formula (7);
   (iv) subjecting the tetrahydrofuran compound of the following formula (7) to Wittig reaction to obtain a compound of the following formula (8);
   (v) subjecting the compound of the following formula (8) to hydroboration followed by oxidation to obtain a compound of the following formula (9); and
   (vi) oxidizing a hydroxyl group of the compound of the following formula (9):

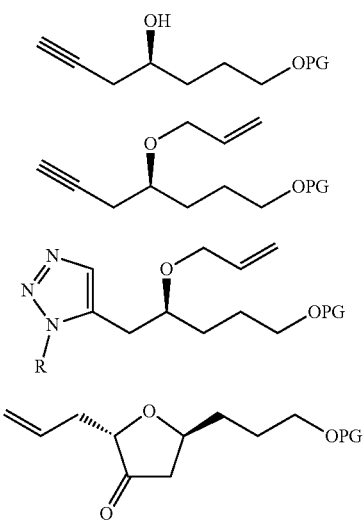

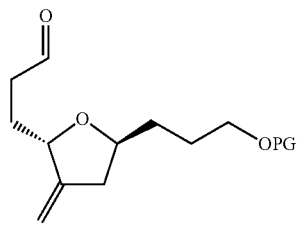

wherein,
R is an arylsulfonyl group substituted or unsubstituted with $C_1$-$C_6$ alkyl group, and
PG represents a protecting group.

2. The process according to claim 1, wherein
R is p-toluenesulfonyl, and
PG is t-butyldiphenylsilyl.

3. The process according to claim 1, wherein
the reaction of step (i) is performed in the presence of sodium bis(trimethylsilyl)amide and n-tetrabutylammonium iodide.

4. The process according to claim 1, wherein
the reaction of step (ii) is performed in the presence of n-butyl lithium.

5. The process according to claim 1, wherein
the denitrification and rearrangement of step (iii) are performed in the presence of a rhodium catalyst.

6. The process according to claim 1, wherein
the hydrolysis of step (iii) is performed in the presence of alumina ($Al_2O_3$).

7. A process for preparing a compound of the following formula (1), which comprises the steps of:
   (iii) subjecting a triazole compound of the following formula (6) to denitrification and rearrangement followed by hydrolysis to obtain a tetrahydrofuran compound of the following formula (7);
   (iv) subjecting the tetrahydrofuran compound of the following formula (7) to Wittig reaction to obtain a compound of the following formula (8);
   (v) subjecting the compound of the following formula (8) to hydroboration followed by oxidation to obtain a compound of the following formula (9); and
   (vi) oxidizing a hydroxyl group of the compound of the following formula (9):

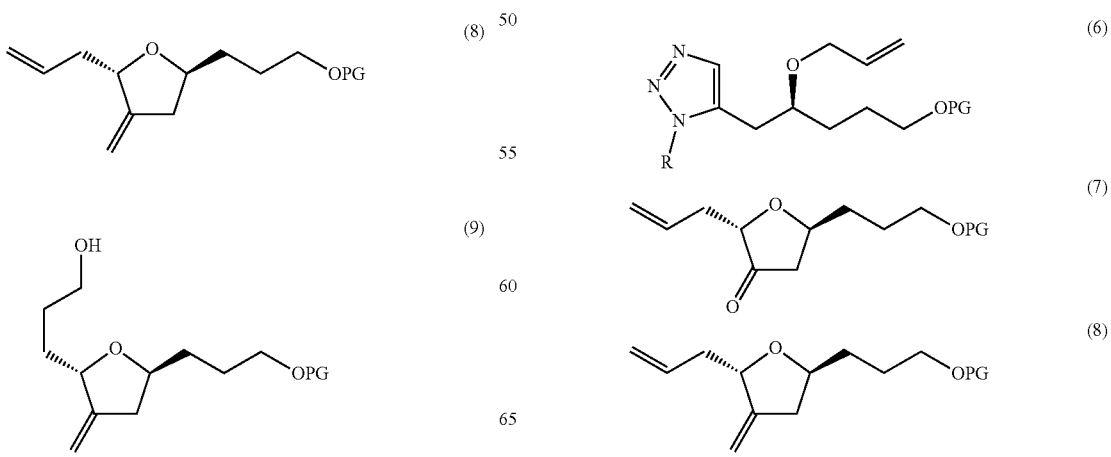

-continued
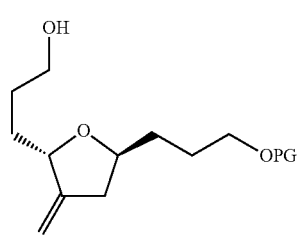
(9)
(1)
wherein,
R is an arylsulfonyl group substituted or unsubstituted with $C_1$-$C_6$ alkyl group, and
PG represents a protecting group.
8. The process according to claim 7, wherein
R is p-toluenesulfonyl, and
PG is t-butyldiphenylsilyl.
* * * * *